US005571189A

United States Patent [19]
Kuslich

[11] Patent Number: 5,571,189
[45] Date of Patent: Nov. 5, 1996

[54] EXPANDABLE FABRIC IMPLANT FOR STABILIZING THE SPINAL MOTION SEGMENT

[76] Inventor: Stephen D. Kuslich, 2400 Keller Pkwy., Maplewood, Minn. 55109

[21] Appl. No.: 246,959

[22] Filed: May 20, 1994

[51] Int. Cl.⁶ .................................................. A61F 2/44
[52] U.S. Cl. ................................. 623/17; 623/66
[58] Field of Search ..................... 623/5, 4, 8, 17, 623/66

[56] References Cited

U.S. PATENT DOCUMENTS

| | | | |
|---|---|---|---|
| 3,867,728 | 2/1975 | Stubstad et al. | 623/17 |
| 3,875,595 | 4/1975 | Froning | 623/17 |
| 4,655,777 | 4/1987 | Dunn et al. | 623/16 |
| 4,735,625 | 4/1988 | Davidson . | |
| 4,755,184 | 7/1988 | Silverberg | 623/16 |
| 4,863,477 | 9/1989 | Monson . | |
| 4,904,260 | 2/1990 | Ray et al. | 623/17 |
| 4,932,969 | 6/1990 | Frey et al. . | |
| 4,932,975 | 6/1990 | Main et al. | 623/17 |
| 5,015,255 | 5/1991 | Kuslich . | |
| 5,059,193 | 10/1991 | Kuslich . | |
| 5,108,438 | 4/1992 | Stone | 623/17 |
| 5,171,280 | 12/1992 | Baumgartner | 623/17 |
| 5,171,281 | 12/1992 | Parsons et al. . | |
| 5,192,326 | 3/1993 | Bao et al. | 623/17 |
| 5,306,307 | 4/1994 | Senter et al. . | |
| 5,306,308 | 4/1994 | Gross et al. | 623/17 |
| 5,306,309 | 4/1994 | Wagner et al. . | |
| 5,306,310 | 4/1994 | Siebels . | |
| 5,306,311 | 4/1994 | Stone et al. . | |
| 5,314,477 | 5/1994 | Marnay . | |
| 5,314,478 | 5/1994 | Oka et al. . | |

FOREIGN PATENT DOCUMENTS

| | | | |
|---|---|---|---|
| 277282 | 8/1988 | European Pat. Off. | 623/17 |
| 93/016664 | 9/1993 | European Pat. Off. | 623/17 |
| 2639823 | 6/1990 | France | 623/17 |

Primary Examiner—Michael J. Milano
Attorney, Agent, or Firm—Vidas, Arrett & Steinkraus

[57] ABSTRACT

An expandable, porous fabric implant for insertion into the interior of a reamed out disc which is packed with material to stabilize the spinal segment. The fabric pores allows for tissue ingrowth through the implant.

3 Claims, 16 Drawing Sheets

Fig. 6
Fig. 7a
Fig. 7b
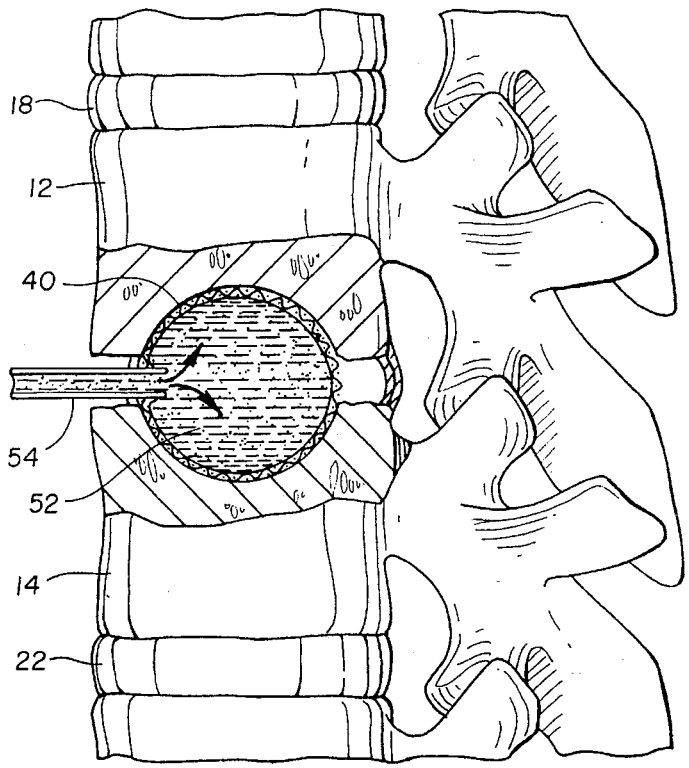
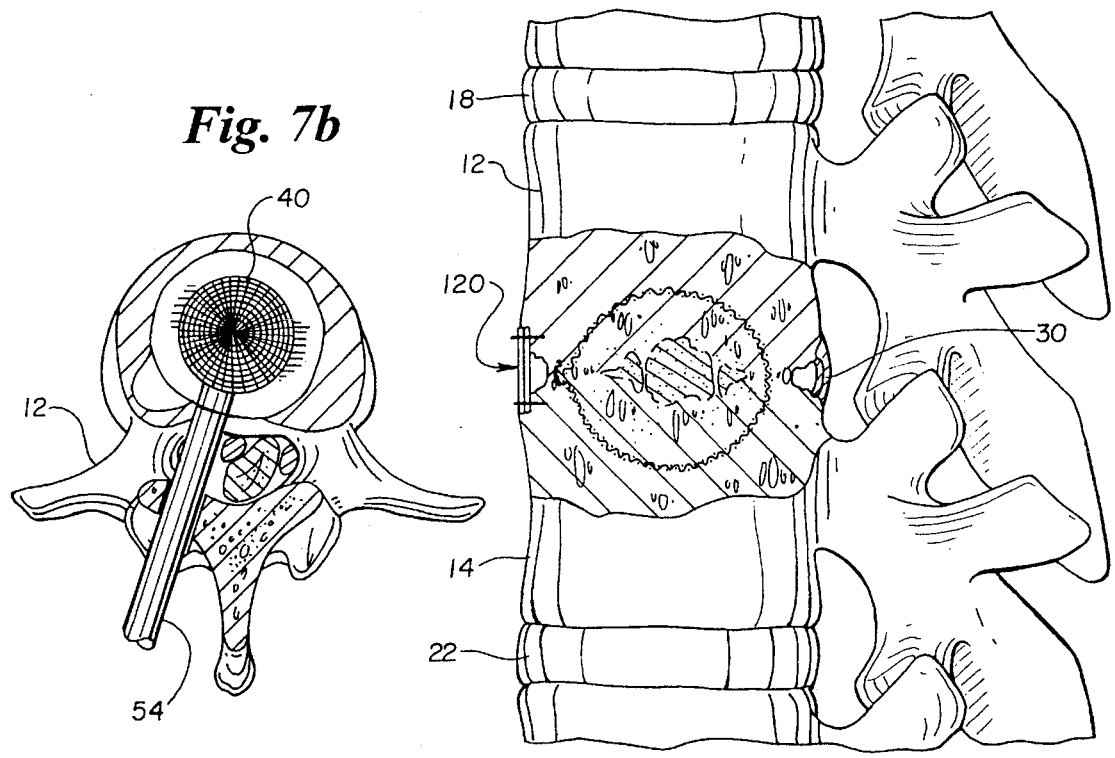

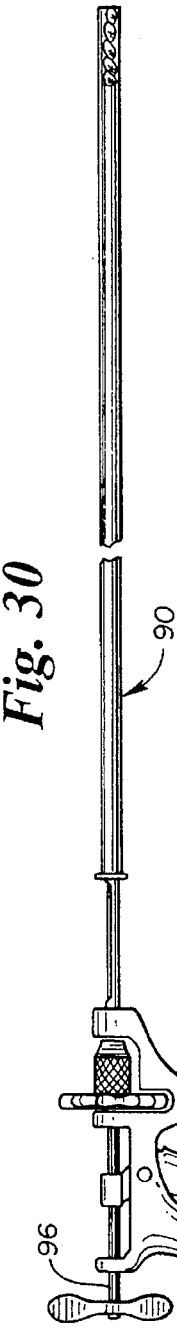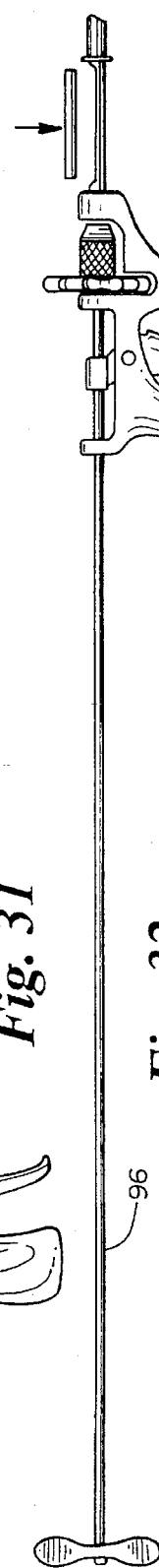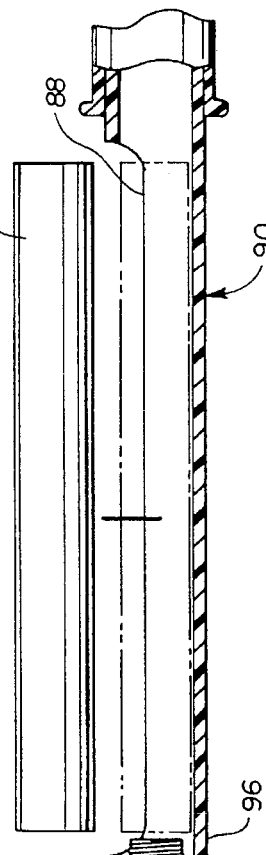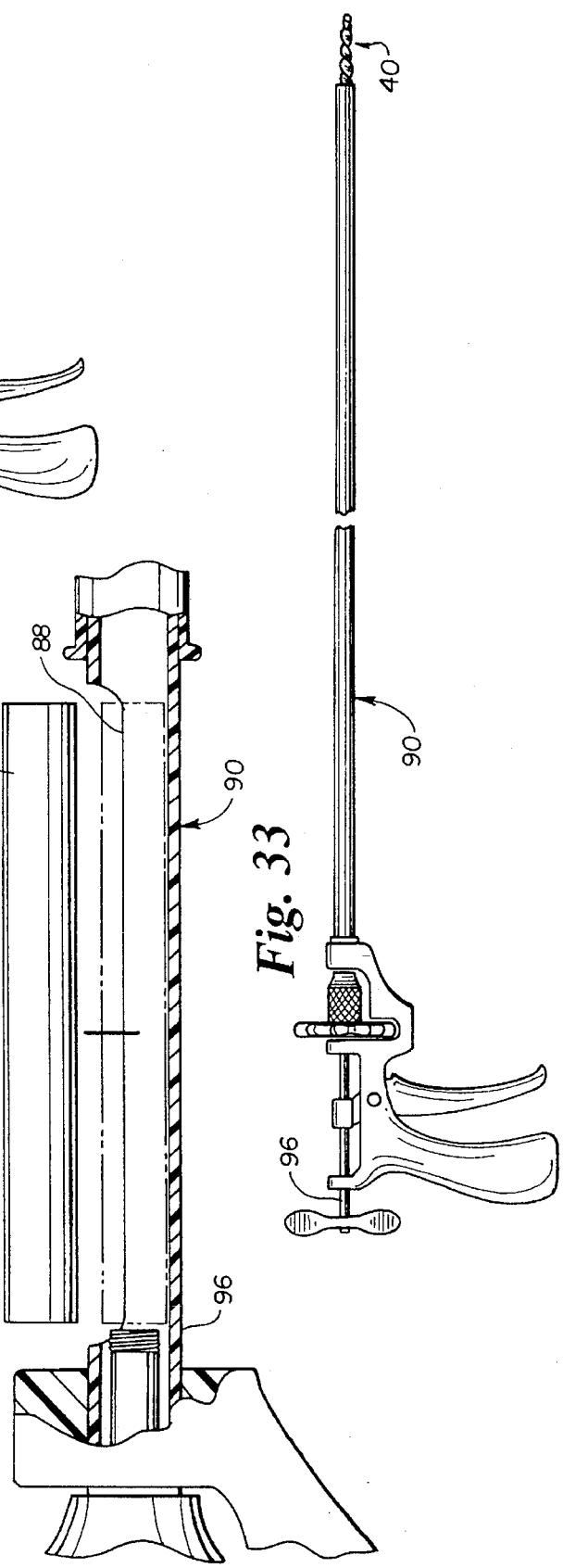

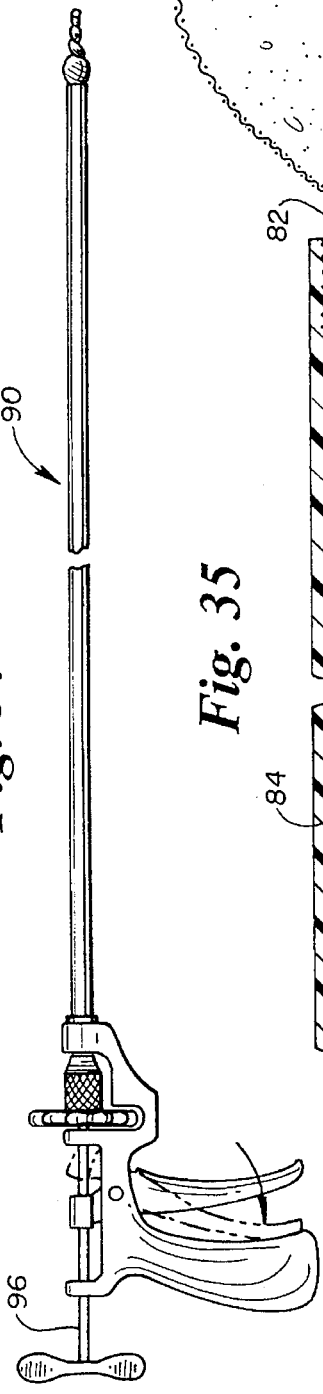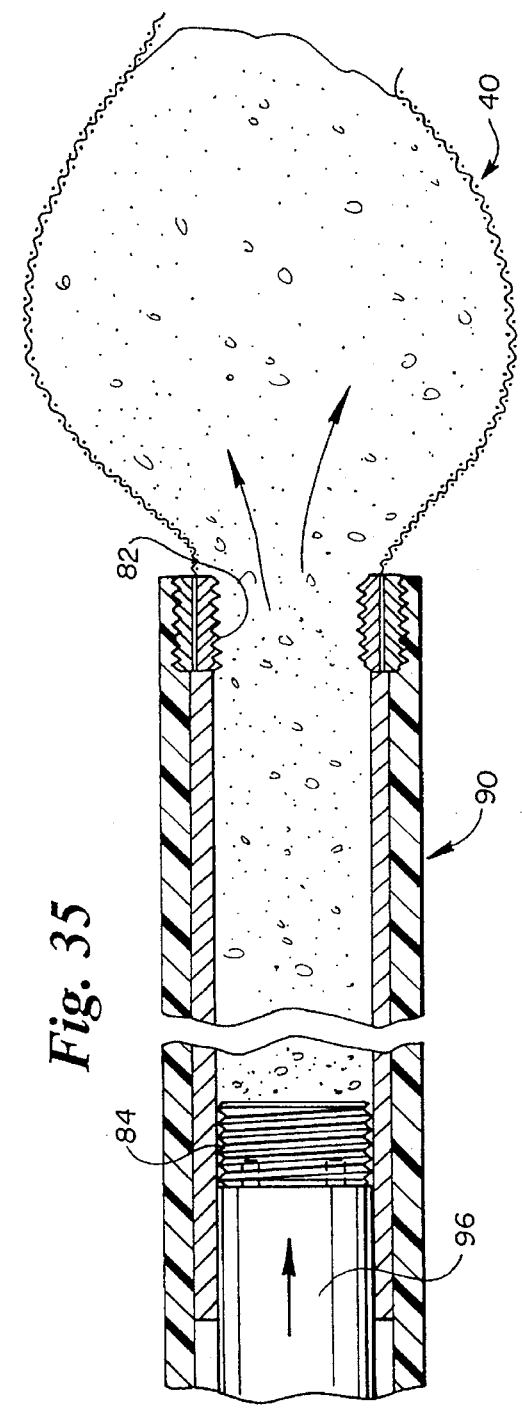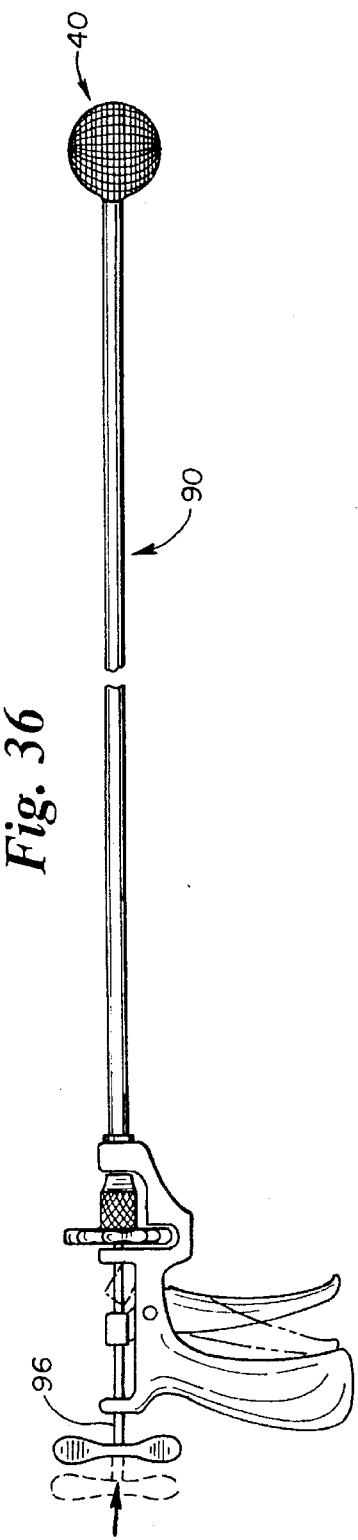

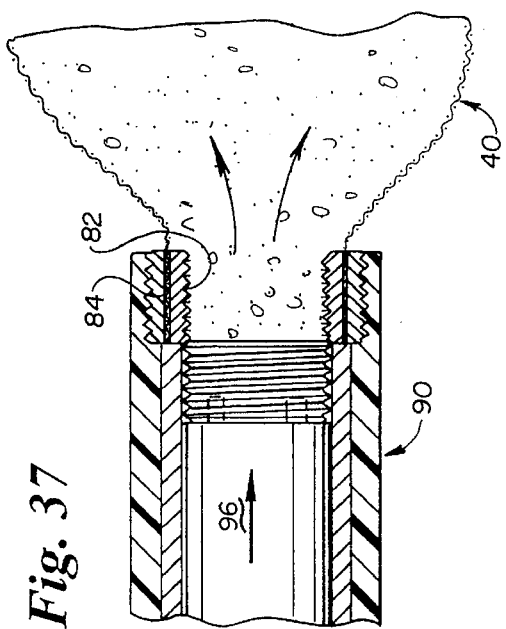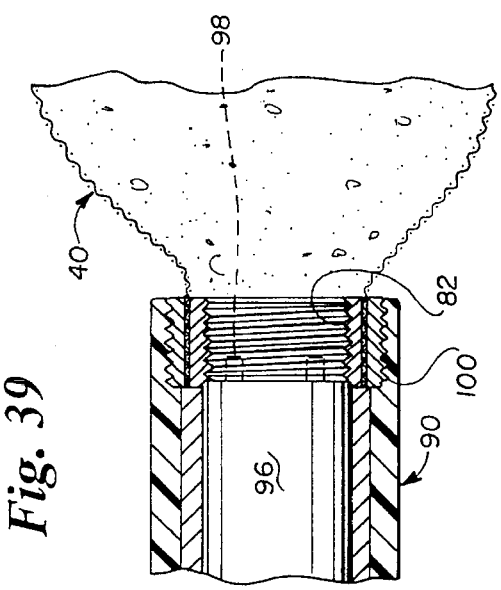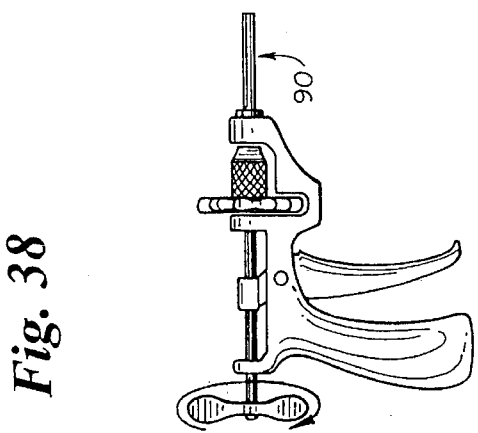

EXPANDABLE FABRIC IMPLANT FOR STABILIZING THE SPINAL MOTION SEGMENT

BACKGROUND OF THE INVENTION

1. Field of the Invention

This invention relates to a method and device for stabilizing a deteriorating spinal motion segment composed of two vertebrae adjacent a disc.

2. Description of the Related Art

Low back pain is a medical condition affecting millions of humans. It is the most common cause of disability for the middle aged working population. In addition to the discomfort and pain experienced by the individual, substantial costs are borne by society, including costs for the diagnosis and treatment, and the cost of payments for disability benefits. Lost productivity is more difficult to quantify, but we know that it is substantial. Any new knowledge that leads to a greater understanding of the causes, prevention, or treatment of the low back pain is a worthwhile and important contribution to the welfare of individuals and society in general. Any intervention that reduces or eliminates symptoms would constitute a significant breakthrough. That discovery would improve the quality of life for countless individuals and reduce the expenditure of scarce societal financial resources.

Recent medical evidence indicates that the symptoms of low back pain are most commonly caused by pathologic changes occurring in what is called the "spinal motion segment." The spinal motion segment consists of a unit of spinal anatomy bounded by two vertebral bodies, containing those bodies and the interposed intervertebral disc, as well as the attached ligaments, muscles, and the facet joints.

The disc consists of the cartilaginous end plates at the top and bottom of the vertebral bones, the annulus fibrosis running circumferentially around the nucleus, and the nucleus itself. In normal discs, the nucleus acts as a damper to cushion applied loads, thus protecting the other elements of the motion segment. The nucleus contains hydrophilic (water attracting) mucopolysaccharides and a small amount of fibrous strands. The nucleus is incompressible. It responds to compression forces (as in sitting, standing walking and lifting) by bulging outward against the vertebral end plates and the annulus fibrosis. Mechanical forces acting on the disc are substantial, i.e. approaching 1000 lbs/in$^2$ when a heavy load is lifted.

The annulus consists of a woven fabric of collagen fibers and a smaller amount of elastic fibers, both of which are extremely strong in resisting tension forces. Unfortunately the annulus is not very strong when it is required to withstand compression and shear forces. The vertebral end plate can deform slightly by bulging into the vertebral bodies, as long as the applied forces are not great, and a long as the force is dampened by the bulging of the annulus.

DISC DEGENERATION

The primary cause of low back pain is degeneration of the lumbar discs. For reasons that are not perfectly clear, many if not most humans develop pathologic changes in the nucleus as they approach middle age. In about one third of individuals, the process is painless. In the other two-thirds, the disease causes pain varying from mild and intermittent to severe and constant. As the nucleus begins to dry up, so to speak, it fragments, and looses its' ability to act as a cushion. This process is usually slow, but may be rapid if the disc is injured by the application of a very great load; as may occur during an accident or by the lifting of a great weight, or as a result of the combination of forces while stooping, bending, twisting or lifting.

This condition of disc dehydration is sometimes called "isolated disc resorption." Dehydration of the nucleus reduces its' ability to act as a cushion. As a result, loads are transferred to the annulus of the disc and to the facet joints. These later structures are not capable of withstanding the applied compression and torsional loads, and they gradually deteriorate. Effects of this process include narrowing of the interspace, bony spur formation, fragmentation of the annulus, fracture and deterioration of the cartilaginous end plates, and deterioration of the cartilage of the facet joints. The annulus and facet joints loose their structural stability while subtle but pathologic motions occur between the spinal bones—a condition known as "segmental instability" occurs. The process is sometimes referred to as the "degenerative cascade." Breakdown products of the disc and facet joint, including macroscopic chunks, microscopic particles, and noxious chemical substances build up. These breakdown products stimulate sensitive nerve endings in and around the disc, producing low back pain and sometimes, sciatica. Affected individuals experience muscle spasms, reduced flexibility of the low back, and pain when ordinary movements of the truck are attempted; e.g. stooping, bending, lifting, standing, walking, or even rolling over in bed. Simple and effective cures do not exist. The process is irreversible. Fortunately, in some if not most cases, as the disease continues to run its' course, the body eventually re-stabilizes the disc by stiffening the joints of the motion segment. Then the pain may decrease or cease altogether. Unfortunately, in a significant number of individuals (10–15%) the restabilization process does not take place. Even in the group where restabilization occurs, the process requires several years or even decades to complete. During that time the patients often experience recurrent bouts of disabling pain.

Direct observations by other investigators during the performance of lumbar procedures have confirmed the sensitivity of certain lumbar tissues. In addition, the most extensive direct observations of these phenomena to determine the exact source of lumbar pain have been performed and published by the inventor.

Clinically significant low back pain is derived, in the main, from pathologic stimulation of these, and only these structures: 1) the vertebral end plate, 2) the outer layers of the annulus fibrosis, and to a lesser extent, 3) the capsule of the facet joint. All of these structures produce typical low back pain when they are subjected to mechanical forces that exceed a certain threshold. In addition, it is likely, based on recent investigations into the biochemical milieu of the motion segment, that certain local chemical abnormalities may play a role in lowering the threshold for the stimulation of pain transmitting fibers.

Surgeons have devised several methods to stabilize the motion segment. These methods fall into the following general categories:

1) Decompression of the spinal canal by removal of part or all of the remaining nucleus, sometimes called "partial discectomy" or "discectomy."

2) Decompression of the spinal canal by removal of non-nuclear tissues., e.g. ligamentum flavum removal or bone removal, sometimes called "laminotomy" or "laminectomy."

3) Spinal fusion by a great variety of techniques.

Fusion consists of the preparation of the existing bone surfaces by decortication (scraping the surface of the bone) and the deposition of additional bone onto the prepared surface. The fusion may be posterior (from the back side of the patient) or anterior (from the front side of the patient). The bone may be cortical (hard bone) or cancellous (soft bone) or a combination of the two (cortico-cancellous). Great controversy exists regarding the preferred method of performing these fusions for various conditions of the spine. Sometimes non biological material are used to augment and support the bone graft (fixation systems). Sometimes the fixation is performed from the posterior route (posterior fixation), or from the anterior route (anterior fixation), or even both sides (anterior posterior fixations or circumferential fusion).

Bagby was the first to describe a method of stabilizing the spine by interbody fusion using a rigid, hollow housing containing bone graft, wherein the bone graft is contained entirely within the housing or implant. My modification of that method of spinal fusion (U.S. Pat. No. 5,015,255) attempts to accomplish a fusion with less damage to surrounding tissue and earlier stabilization of the motion segment, and using special tools for safe insertion. Even that method and many others similar to it require the placement of devices from both sides of the spine and the installation of a fairly large implant that will not fit through small portals. Examples include the implants described by Brantigan in U.S. Pat. Nos. 5,192,327; 4,878,915; 4,834,757 and 4,743,256. Two types of expandable, bone containing implants have been described. One is that of Kuslich, U.S. Pat. No. 5,059,193 consisting of a cylindrical device that expands to from a reinforced arch when it is expanded in the interbody space. Kuslich U.S. Pat. No. 5,059,193 uses a netting to prevent its ribs from sinking into soft vertebral bone. The other uses a memory metal (nickel-titanium alloy) that expands in the interspace when the temperature changes. Turn buckle type implants of Razian, U.S. Pat. No. 4,401,112 and Ogilvie, U.S. Pat. No. 4,636,217 expand, but do not contain graft within a housing.

Arthur Steffee describes an artificial disc with an elastomeric core between flat rigid plates in U.S. Pat. No. 5,071,437. An artificial disc using a spring is described in Kostuik et al, U.S. Pat. No. 4,759,769. Casey Lee et al, in U.S. Pat. Nos. 5,171,281 and 4,911,718 describe intervertebral disc spacers. Ray et al in U.S. Pat. No. 4,904,260 describes a disc capsule which must block passage of human cells. Bao et al in U.S. Pat. No. 5,192,326 describes a replacement for the nucleus filled with hydrogel beads. None of these encourage or allow through-growth of living cells.

The art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 C.F.R. §1.56(a) exists.

SUMMARY OF THE INVENTION

The invention provides a flexible fabric implant that may be inserted into a cavity formed in a degenerating disc. The flexibility of the bag allows it to be inserted through a relatively small opening in a disc. The bag is then positioned so its fill opening may receive biological fill material. This material is packed into the flexible bag, causing the bag to expand and conform to the cavity formed in the disc. Fill material is added until enough material is present to "inflate" the disc to the desired position. At this time, the bag fill opening is closed to prevent egress of the fill material.

The relatively open weave of the bag allows the normal movement of body fluids through the bag. It also allows the ingrowth of bony trabeculae and fibrous elements into and through the flexible bag. It does not allow the egress of the nonliquid fill material.

In preferred forms of the invention, the flexible bag includes an equatorial band which is substantially less flexible than the remainder of the bag. This controls the shape of the bag and pressures within the bag by means of applying tension on the band and thereby restricting equatorial expansion while encouraging polar expansion along the long axis of the spine.

BRIEF DESCRIPTION OF THE DRAWINGS

A detailed description of the invention is hereafter described with specific reference being made to the drawings in which:

FIG. 6 is a fragmentary view thereof showing inflation of the device being inflated with fill material;

FIG. 7a is a fragmentary view thereof showing a partial healing spinal motion segment after the method is complete;

FIG. 7b is a transverse section showing insertion of the bag from another direction;

FIG. 27 shows a cartridge loaded with fill material for use in injecting material into the bag as in FIG. 21;

FIG. 28 is a cross-sectional view through lines 28—28 of FIG. 27;

FIG. 29 shows a press with the cartridge of FIGS. 27, 28 being loaded with material;

FIG. 30 shows a device for accepting a cartridge of FIG. 27 to inject material;

FIG. 31 shows the device of FIG. 30 with plunger withdrawn;

FIG. 32 is a partial enlarged view of FIG. 31 showing insertion of a cartridge;

FIG. 33 shows injection of material through the device;

FIG. 34 shows filling of the bag;

FIG. 35 shows a cross-section of the end of the device of FIG. 34 filling of the bag;

FIG. 36 shows the bag inflating;

FIG. 37 shows the bag nearly fully inflated with the closure plug about to engage;

FIG. 38 shows rotation of the insertion tool plunger to rotate the closure plug;

FIG. 39 shows the closure plug secured;

DESCRIPTION OF THE PREFERRED EMBODIMENTS

Figure 3:
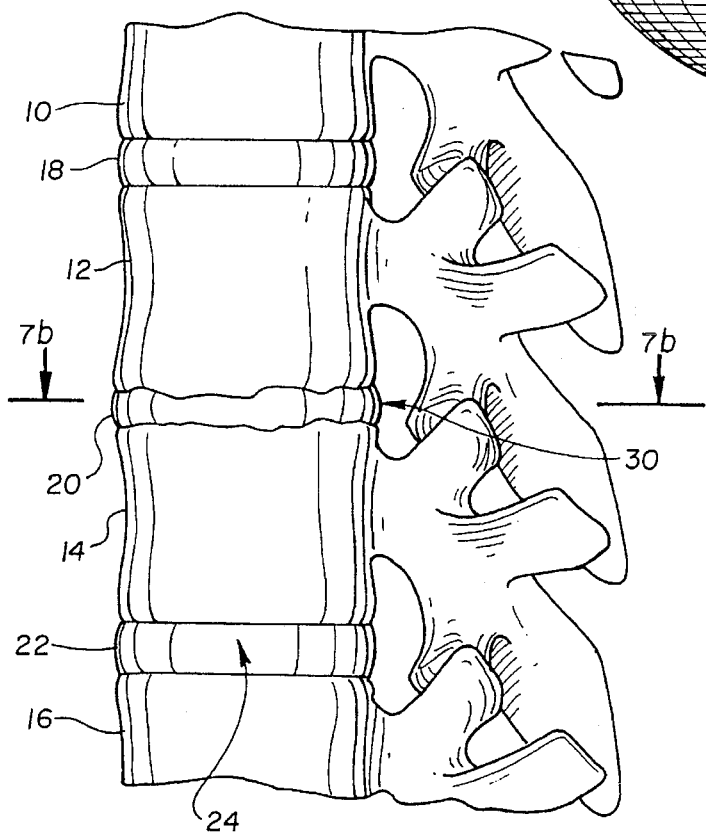
FIG. 3 is a fragmentary view of a spinal column unoperated spine showing normal and pathologic discs.
Figure 4:
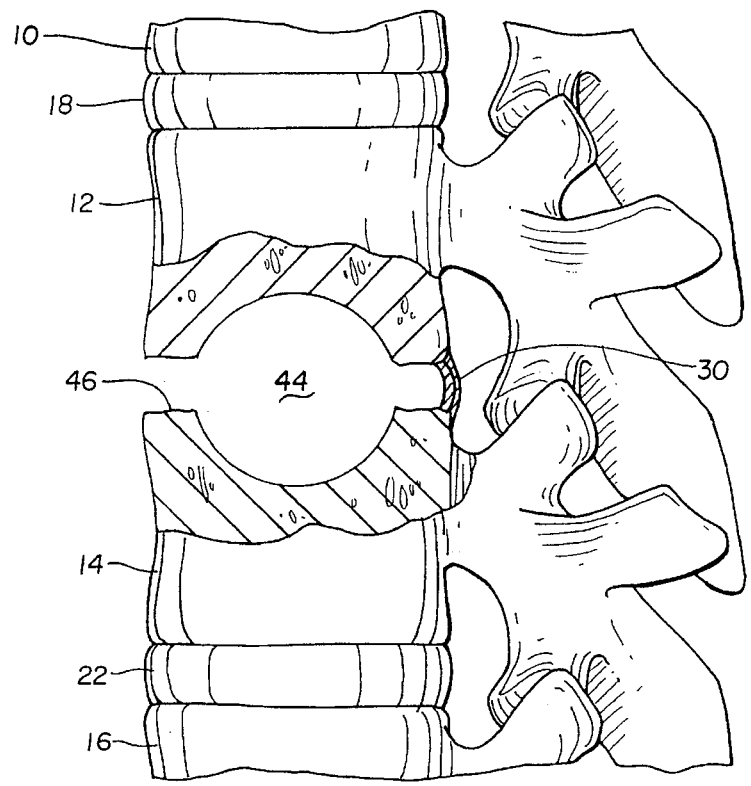
FIG. 4 is a fragmentary view of a spinal motion segment after disc debridement is used, reamed out with parts cutaway.

With reference to the Figures, FIG. 3 shows typical spinal motion segments, with lumbar vertebrae 10, 12, 14 and 16 shown, separated by three discs 18, and 22. As depicted, disc 20 is deteriorating. Each disc includes a nucleus 24, top and bottom end plates 26.28 and an annulus fibrosis 30.

The implants of the invention offer a third method of expansion by means of injection of material into a tension-resisting fabric bag that expands to predetermined dimensions when filled to full capacity. In addition, the invention may consist of materials that are eventually resorbed by the body, leaving no trace of foreign substances.

Most of the factors that are known to produce or potentiate pain production can be explained by the pathologic disc degeneration and the segmental instability that follows its appearance. Most of the previously described methods of spinal stabilization have been developed with the expressed purpose of treating the condition of disc degeneration only after irreversible changes have taken place in the other tissues of the motion segment.

Methods that will accelerate the normal restabilization process ought to be implemented during the early phases of disc degeneration, before severe pathologic changes occur in the surrounding tissues, and before the patient develops the physical and psychological disabilities associated with the normal course of the condition. For instance, the methods described here may be used during routine removal of disc herniations in order to preempt the further degeneration and resulting back pain and instability that frequently results from these types of procedures. Sprangford et al reported 31.5% failure rates in terms of continued low back pain in spite of good results for sciatica relief when disc herniations were treated by laminectomy. Acta. Orthop. Scanda, 1972, 142 (Suppl.), 1–95.

The most often performed spinal fusions are classified as postero-lateral or interbody in order to specify the area of decortication and bone graft application. Postero-lateral grafting is often effective but its fusion rate is low when more than one level is fused and the operation requires a large exposure with resultant high blood loss, long recovery time, long operation times and frequent episodes of lingering pain in spite of apparently solid fusion.

The methods and spinal implants of the invention are designed to re-stabilize the spinal motion segment in a rapid and effective manner. They should lead to relief of the low back pain and a concomitant improvement in the quality of life for the patient. In addition, one might reasonably expect that these methods and implants will also decrease the cost of medical care and a reduce the disability-associated expenses to society.

Description of the Devices

Figure 1:
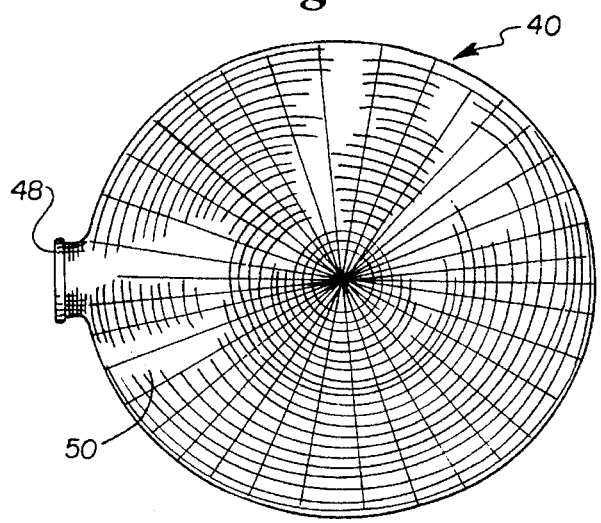
FIG. 1 is a top plan view of the device of the invention.
Figure 2:
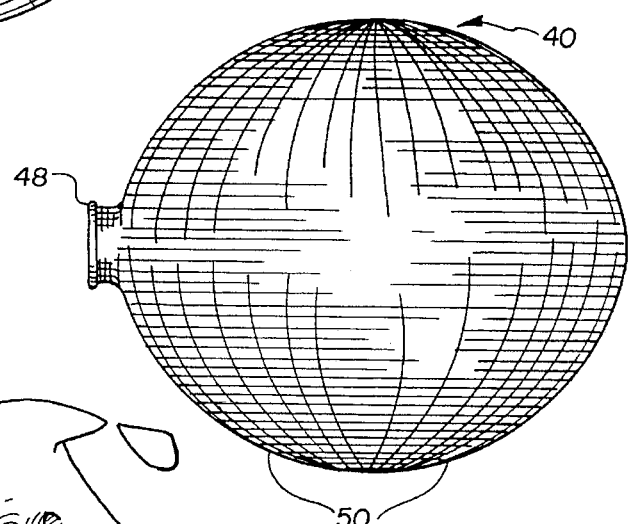
FIG. 2 is a side elevational view thereof the inventive device.

The inventive implant 40 consists of a small (approx. one to four cm diameter) fabric bag, roughly spherical in shape, although elliptical shapes and other geometric shapes may be used. (See FIGS. 1, 2). One additional shape consideration would be the provision for an enlarged or constricted and/or less compliant equatorial band 42 that would confine the internal cavity more securely at the center or equator of the implant 40, at the point where the implant 40 is opposed to the annular wall, which is less rigid than the cancellous bone wall of the carved out cavity 44 of the vertebral bodies. The bag is pliable and malleable before its interior space is filled with the contents to be described. While in this initial condition, the bag may be passed, uninflated, through a relatively small tube or portal, perhaps one cm or smaller in diameter. (See FIGS. 5, 21). This feature is important because access to the intervertebral disc is limited by anatomy and therefore safety considerations direct us to use the smallest possible portal of entry.

The bag 40 is constructed in a special and novel way. The bag fabric may be woven or form-molded to a density that will allow ingress and egress of fluids and solutions and will allow the ingrowth and through-growth of blood vessels and fibrous tissue and bony trabeculae, but the weave is tight enough to retain small particles of enclosed material, such as ground up bone graft, other tissues or solid pieces of bone inducing material such as hydroxyapatite or other biocompatible materials known to promote bone formation. Generally, the pores of the fabric will have a diameter of about 0.25 mm to about 5.0 min. The size is selected to allow tissue ingrowth while containing the material packed into the bag.

The fabric is light, biocompatible, flexible and easily handled, but its fabric is very strong in terms of resisting tension, and thus unlikely to rip or tear during insertion and inflation. When the device is inflated, the device expands to a predetermined shape, and in doing so, it fills a previously excavated space 44 between the vertebral bodies. This filling results in the separation of the vertebral bodies along the cranial-caudal axis, lengthening and tightening the fibers of the annulus fibrosis 30, and in the process, as we know from the teachings of Cloward and Bagby, results in the stabilization of the spinal motion segment. (See FIGS. 6, 7a).

The use of the term "fabric" herein is meant to include the usual definition of that term and to include any material that functions like a fabric. That is, the "fabric" of the invention must have a plurality of pores through which material and fluid flow is allowed under the terms as described, and the "fabric" must be flexible enough to allow it to be collapsed and inserted into an opening smaller than the inflated bag size.

Accordingly, the "fabric" bag or implant 40 may be formed from a polymeric balloon to which a plurality of perforations are formed or added. It need not be woven and may be molded or otherwise formed as is well known in the art. The preferred material may provide the ability to tailor bioabsorbance rates. Any suture-type material used medically may be used to form the implant 40. The implant may be formed of plastic or even metal. The fill opening may be a bushing 72 that could be bioabsorbable such as hydroxyapatite or it could be a plastic or metal. The bag 40 could be formed from a solid material to which perforations are added. The implant 40 may be partially or totally absorbable, metal, plastic, woven, solid, film or an extruded balloon.

The use of external electrical fields to stimulate bone growth and repair is well known. It is also possible to include metal or other conductive fibers 50 in the walls of the bag 40 such that an external electrical field could amplify and stimulate bone union at the situs of the bag.

As will be described, it is anticipated that the bag 40 will be preferably used in surgery in spines of humans as well as other animals. Accordingly, the material of bag 40 should be biocompatible.

SURGICAL METHOD

1. Formation of Entrance Bore

As indicated, the bag 40 is preferably used in spinal stabilization surgery. FIG. 3 of the drawings shows vertebrae 12 and 14 separated by disc material 20 that is pathologic and in need of repair.

Figure 5:
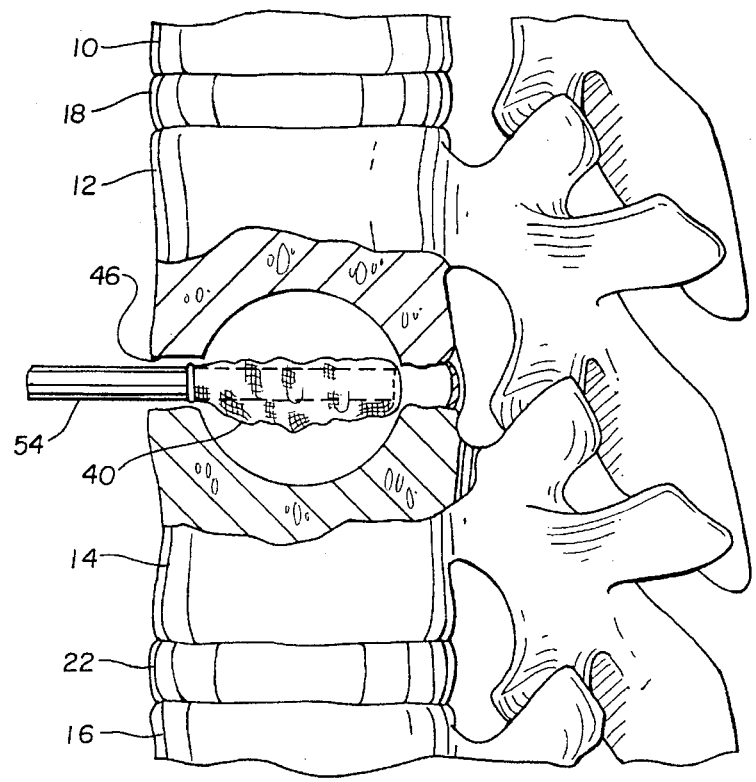
FIG. 5 is a fragmentary view thereof with insertion of the device of the invention.
Figure 8:
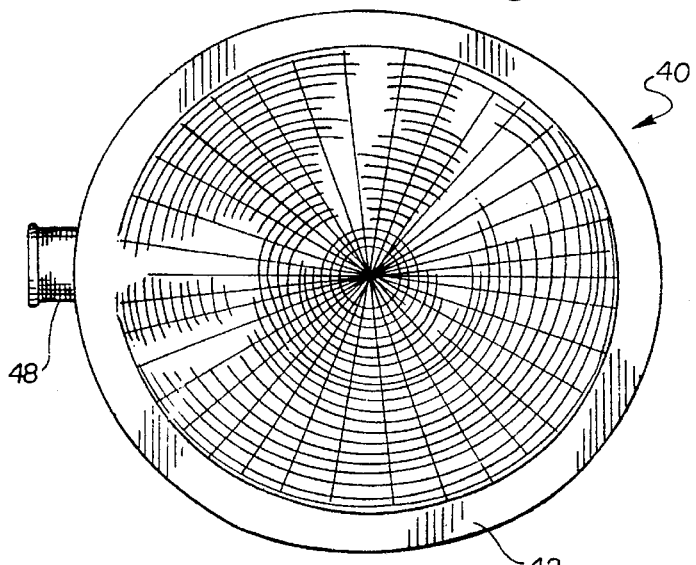
FIG. 8 is an embodiment including an equatorial band.
Figure 9:
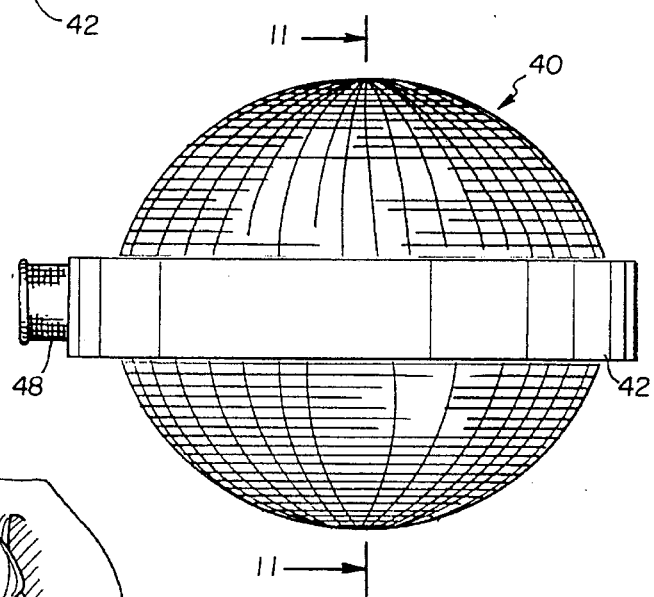
FIG. 9 is a side elevational view thereof of the embodiment of FIG. 8.
Figure 10:
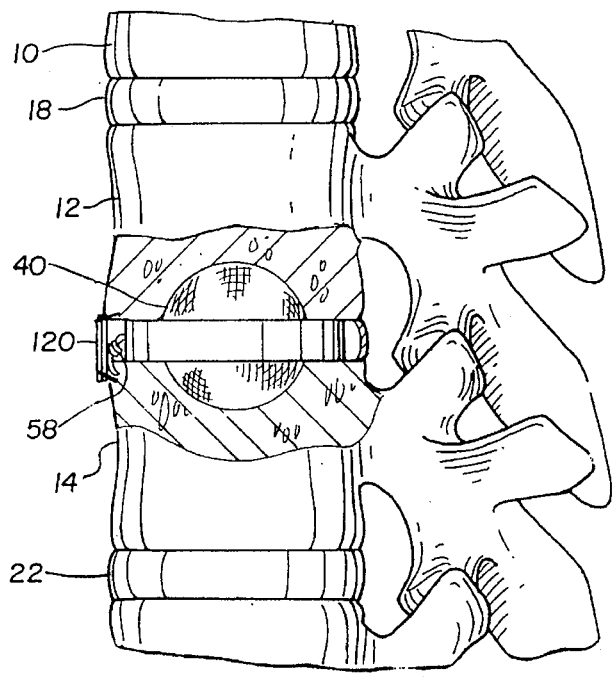
FIG. 10 is a fragmentary view thereof showing the device of FIG. 8 in position.

The cavity 44 in the disc 20 may be formed in accordance with the methods and devices of U.S. Pat. No. 5,059,193, the disclosure of which is incorporated herein by reference. Generally, after identifying a diseased disc 20, the surgeon forms a bore 46 through the annulus 30. The bore 46 is formed through any conventional means. The bore is sized such that the diameter of the bore 46 is approximately sized to be the external diameter of the implant body 40 when in the relaxed or first state as shown in FIG. 5. The depth of the bore 46 is controlled so that the axial length of the body 40 may be fully inserted within the bore, with the body 40 fully located between opposing vertebrae 12, 14.

While the diameter of body 40 and bore 46 will vary from patient to patient, there is a practical maximum size of the diameter of bore 46 for any given patient. This maximum is attributed to the fact that too large of a drill bit cannot be passed through the patient's body and placed against disc tissue. If too large a drill bit is used, the size of the bit will interfere and possibly damage other anatomical parts, such as important blood vessels, nerves, etc.

A typical selected diameter of body 40 (when in the first state) and bore 46 is preferably about 12 mm. This diameter is selected for bore 46 to cut through disc material separating the fourth and firth lumbar vertebrae in a human spine in a typical adult human male. The depth of the intervertebral space between the fourth and fifth lumbar vertebrae in an adult human male (measured as the anterior-posterior dimension of the vertebrae) is commonly about 35 mm. As a result, a preferred length of body 40 will be about 25 mm so that the body 40 may be fully received within and between opposing vertebrae.

It will be appreciated that the foregoing dimensions and descriptions have been given with respect to a particular vertebrae location in the spine of an adult human male. It is anticipated the present implant and method could be used on any animal spine. Accordingly, the dimensions of the bag 40 and entrance bore 46 will vary proportionately with increases or decreases in spinal anatomy between different animal types. Also, in humans, the dimension will vary with numerous factors, including anatomic region of the spine, age and sex. For example, the implant and surgical method is not limited to the lumbar region, and may be utilized in other regions of the spine where vertebrae dimensions may be different than those described. Therefore, several different sizes of the bag 40 are anticipated so a surgeon can select the optimum bag 40 for a given patient.

2. Formation of Enlarged Chamber

With the entrance bore 46 formed as described, the surgeon then cuts a hollow chamber 44 between the opposing vertebrae 12 and 14. The chamber 44 is sized to be complementary to the exterior dimensions of the implant 40 in the enlarged state.

Since the chamber 44 has greater volume than a bore 46, the cutting of chamber 44 removes greater amounts of disc material and exposes a greater surface area of the opposing vertebrae bone material. The exposure of the additional surface area increases the probability of successful grafting between the opposing vertebrae 12, 14.

The formation of the enlarged spherical chamber 44 can be formed through any suitable technique. Preferably, the chamber 44 is formed through the use of an intervertebral reamer such as that shown and described in U.S. Pat. No. 5,015,255 and copending U.S. patent application Ser. No. 07/350,050, filed on May 10, 1989, which names myself and James D. Corin as joint inventors.

The diameter of the chamber 44 (and hence, the maximum allowable diameter of the expanded bag 40) is selected to provide a clearance so that the chamber 44 is not cut through the sides of the vertebrae. This diameter will vary from patient to patient, and between locations in the spine. However, to provide a clearance of about 5 to about 11 mm of the sides of the vertebrae, the chamber is preferably held to a maximum diameter of about 20 to about 30 mm.

3. Insertion and Expansion of Implant

With the enlarged chamber 44 so formed, the surgeon places bag 40 in the collapsed, unexpanded state into bore 46 and into cavity 44. (See FIG. 5). The fill opening 48 of the bag 40 is positioned in bore 46.

In FIG. 5, an unexpanded bag 40 is shown inserted within an enlarged chamber 44. In the position shown in FIG. 5, the bag 40 is not urging vertebra 12, 14 apart. Accordingly, the annulus 30 (the fibrous outer circumferential portion of disc 20) connecting the vertebra 12, 14 is shown in a relaxed or unstretched state.

With the bag 40 so inserted, the surgeon then fills the bag or implant 40 until inflated to the desired extent to cause the annulus to stretch out and re-establish the proper distance between the vertebrae 12, 14.

The surgeon continues to insert material until the bag 40 is expanded to the fully expanded state. As it expands, the outer surfaces of the bag 40 abut against the opposing surfaces of the vertebrae 12, 14. Continued expansion of the bag 40 causes the vertebrae 12, 14 to stretch apart slightly. This stretching acts to tighten the annulus 30 of disc 20, which has not been removed through the formation of bore 46 and chamber 44. Those skilled in the art will recognize the annulus 30 as being the fibrous outer circumferential portion of the disc 20. The stretching and tightening of the annulus provides initial stabilization between the opposing vertebrae. So that stretching will occur, the external dimensions of chamber 44 are preferably sized to be about 3 mm less than the external dimensions of the bag 40 measured in the fully expanded state. With the bag 40 fully expanded, the surgeon must close the bag opening 48 to prevent egress of the fill material.

Figure 11:
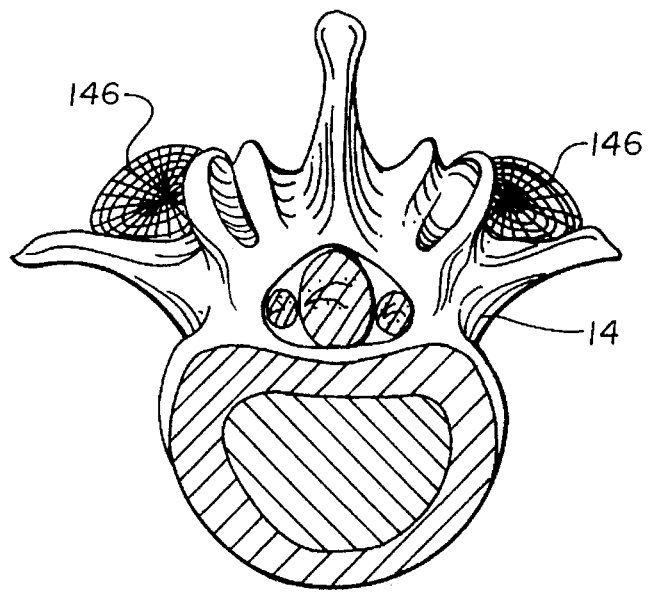
FIG. 11 is a transverse section showing alternative use of the inventive fabric bags for posterolateral fusion.
Figure 12:
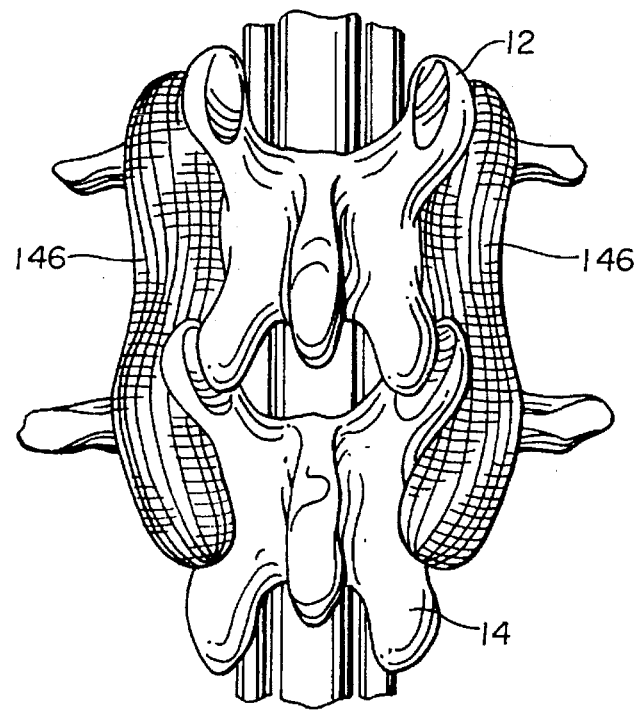
FIG. 12 is a longitudinal view of an alternative use as in FIG. 11 thereof.

In FIGS. 11 and 12, a bag of the invention is depicted as a sausage shaped container 146 which is not implanted into a disc cavity. Rather, one or more of the bag containers 146, prefilled with fill material 52, are positioned against the bone of adjacent vertebrae. The bone may be toughened to a bleeding surface to hasten bone growth into the containers 146. As time goes by, the containers will become very rigid and will be attached via bone ingrowth to both vertebrae where they contact native bone. This will provide a safe, simple fusion. The bags provide containment of the bone-growth material to ensure that the fusion takes place where indicated.

4. Use of a Graft Medium

The chamber 44 is filled with a graft medium 52 to facilitate fusion or fibrous union between the opposing vertebrae 12, 14. The preferred graft medium or fill material 52 would be finely chopped conical or cancellous bone chips for fusion or connective tissue when a fibrous union is desired.

Figure 17:
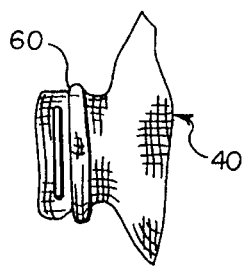
FIG. 17 is a fragmentary view of an alternative closure device method thereof.
Figure 18:
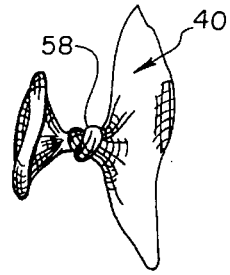
FIG. 18 is a fragmentary view of an alternative closure device thereof.
Figure 19:
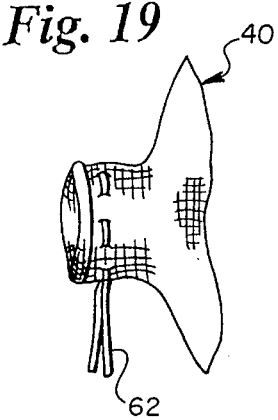
FIG. 19 is a fragmentary view of an alternative closure device.

In the forms of the invention shown in FIGS. 8–10 and 16–29, the bag 40 may be filled by packing the graft medium 52 through a guide tube 54. After the bag 40 is filled as needed, the bag fill opening 48 is closed. FIG. 17 shows a simple staple 60 closure of opening 48. FIG. 18 shows the fill opening 48 closed by tying a knot in the end. FIG. 19 shows a closure using a purse-string 62 closure.

Figure 13:
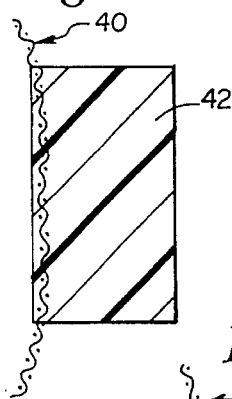
FIG. 13 is a sectional view of an equatorial band of FIG. 8.
Figure 14:
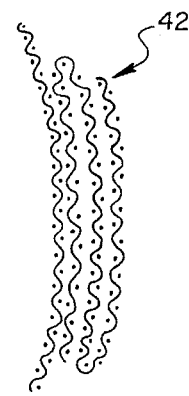
FIG. 14 is an alternate to FIG. 13 in which the equatorial band is simply multiple fabric layers.
Figure 15:
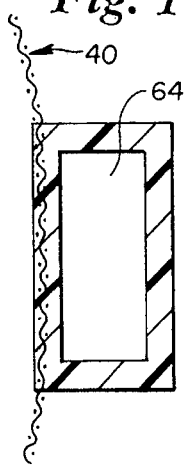
FIG. 15 is a sectional view similar to FIG. 13 in which the equatorial band is hollow.

In the forms in which an equatorial band 42 is employed a different fill opening and closure is possible. FIGS. 13–15 show different ways in which the equatorial band 42 may be formed. As shown, the band 42 may be a molded plastic circumferential band that is stiffer than the bag fabric to which it is attached. In the form of FIG. 15, the band 42 may be hollowed to form a cavity 64 into which bone cement or other material may be added before or after insertion to increase the rigidity of the band. FIG. 14 shows that the band 42 may simply be multiple layers of the fabric which forms the bag.

Figure 16:
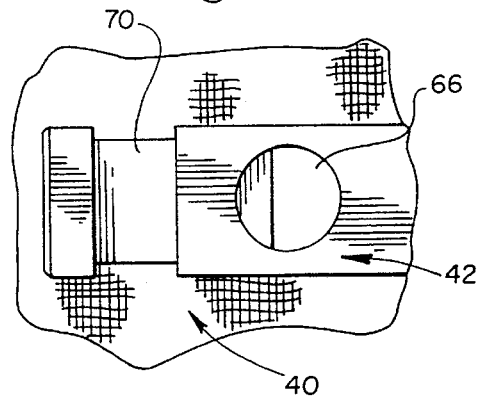
FIG. 16 is a fragmentary view of an alternative closure device method thereof.
Figure 20:
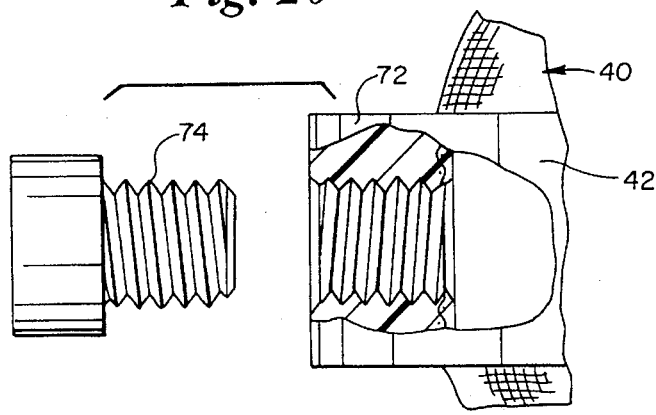
FIG. 20 is a fragmentary view of an alternative closure device.

FIG. 16 shows that the simple band 42 of FIG. 15 may include a fill opening 66 and a slot 64 into which a free end 70 of band 42 may be inserted to close off the opening 66. In a more elaborate closure, band 42 as shown in FIG. 20 may include a molded threaded bushing 72 through which the bag may be filled. Such a threaded bushing 72 is readily closed by a threaded screw 74.

Figure 21:
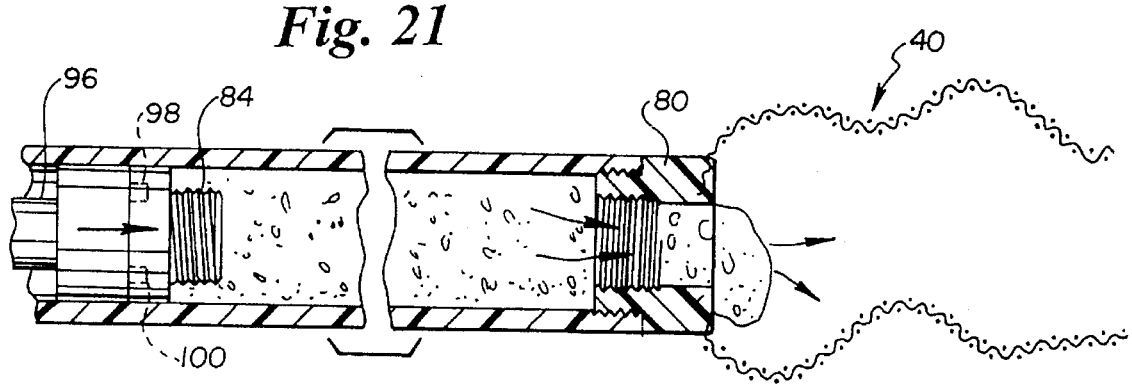
FIG. 21 shows a device for coupling to a fill opening of the device in order to inject in fill material.
Figure 22:
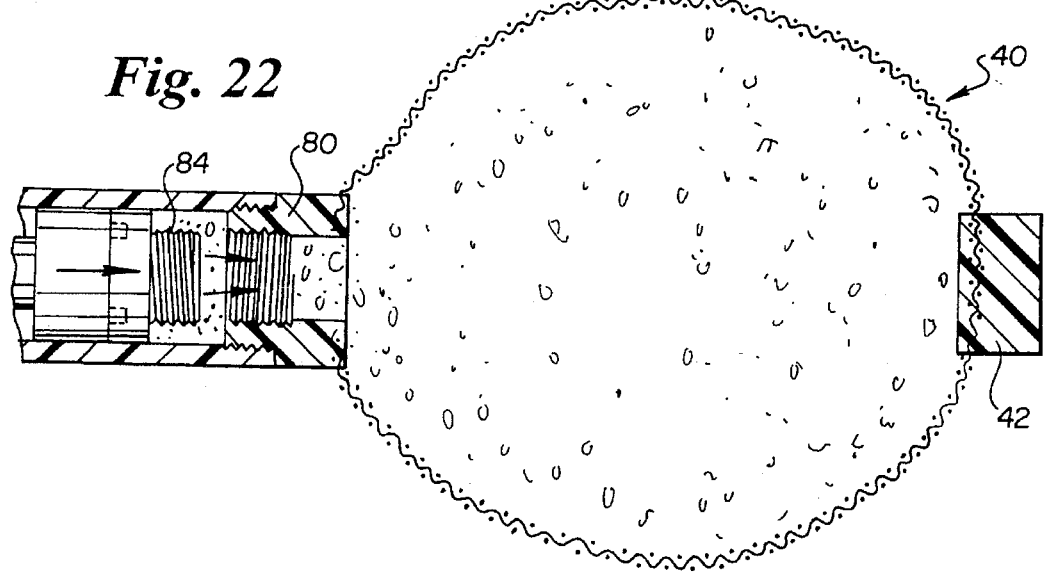
FIG. 22 shows the bag inflating as the fill material is injected from the device of FIG. 21.
Figure 23:
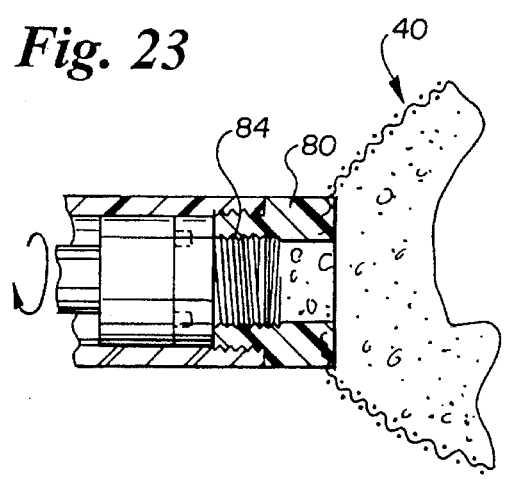
FIG. 23 shows closure of the fill opening with a cap in the fill device of FIGS. 21 and 22.
Figure 24:
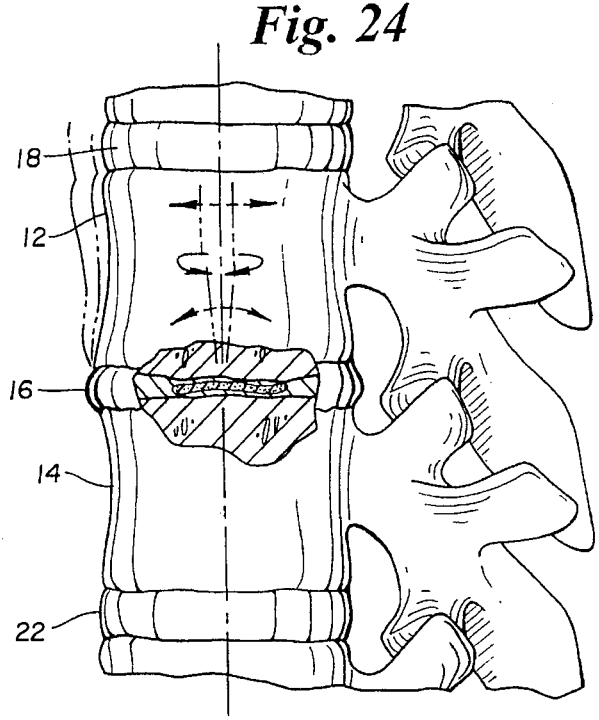
FIG. 24 shows a diseased disc and the ranges of motion.
Figure 25:
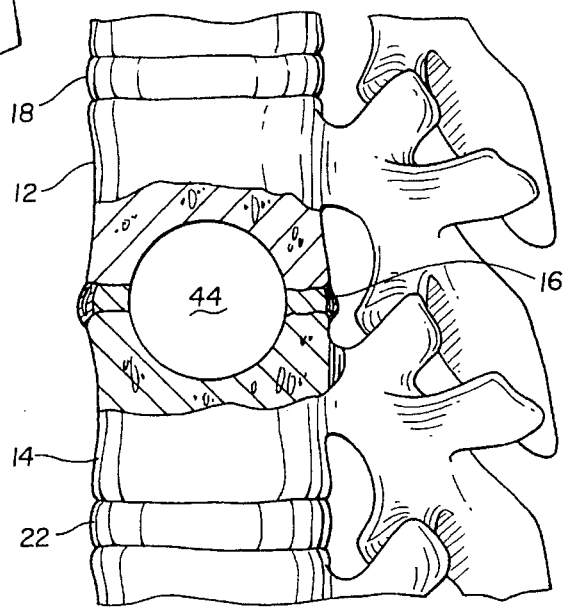
FIG. 25 shows a fragmentary, partially cut-away spinal motion segment restored with the invention.
Figure 26:
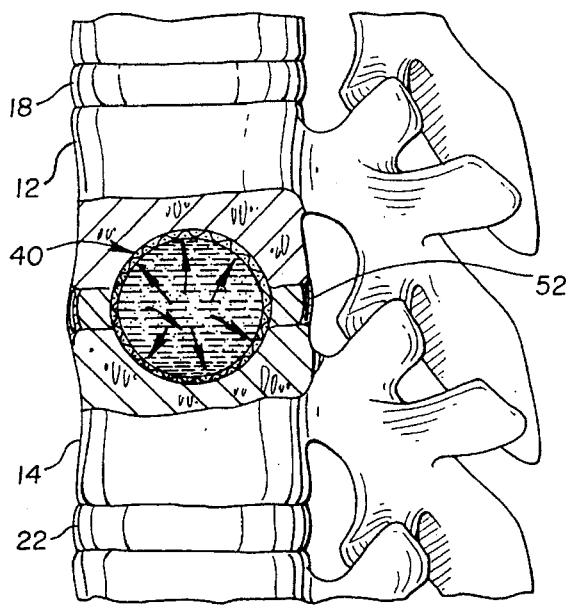
FIG. 26 shows the motion segment of FIG. 25 with biological fluids moving in and out of the bag.

FIGS. 21–23, 30–39 show a method for admitting the graft medium 52 into chamber 44. As shown, the bag 40 includes a threaded fill port 80 which has internal threads 82 to receive a threaded screw 84. Preferably, a device 90 is used to attach to the fill port as shown. Device 90 is prefilled with the graft medium 52 as shown in FIGS. 21–23. In FIGS. 30–39, device 90 may accept a cartridge 92 which may be packed with a press 102. The cartridge 92 would typically include a plurality of side openings 94 to allow fluid and small particles to exit during filling.

The cartridge 92 is inserted into device 90 in an opening 88. The device 90 is threaded or otherwise attached to fill port 80. A plunger 96 pushes the screw 84 toward the internal threads 82, pushing the graft medium 52 into the bag. As the stroke is completed, the plunger 96 is rotated to turn the screw 84 in and seal the implant 40. The plunger may contact the screw via a pair of studs 98 that project into screw recesses 100. The device 90 is then withdrawn.

With the graft medium in place, the surgeon can then close the patient through any suitable technique. The grafting of bone chips results in a fusion between the vertebrae bodies 12, 14. While the fusion process is taking place, the surgeon may monitor the patient's progress if some portion of the implant is radiopaque such as a small wire frame on the leading and trailing edges of the bag. Also, during the fusion process, the bag 40 is self-retaining in a rigid, generally spherical shape due to the fill material therewithin. The rigidity of the enlarged, filled bag 40, together with the stretching of the annulus, provides stabilization between vertebrae 12, 14 during the fusion process.

Figure 40:
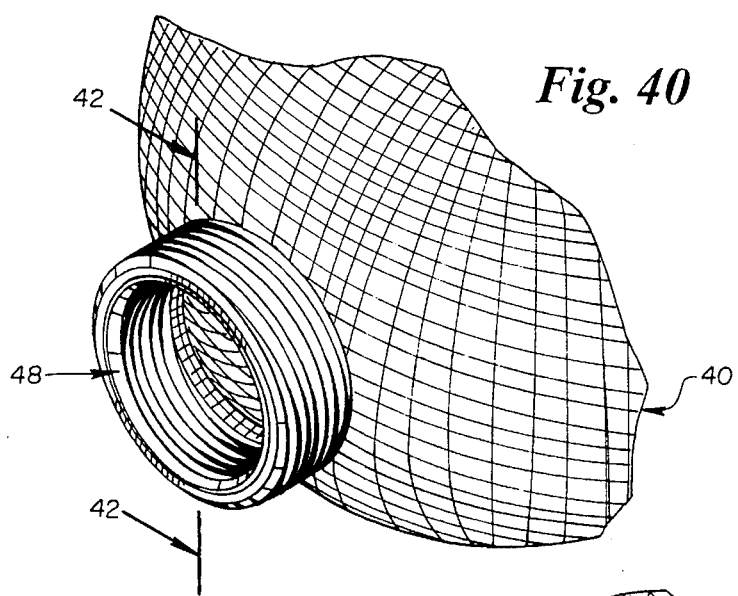
FIG. 40 shows a fill opening construction.
Figure 41:
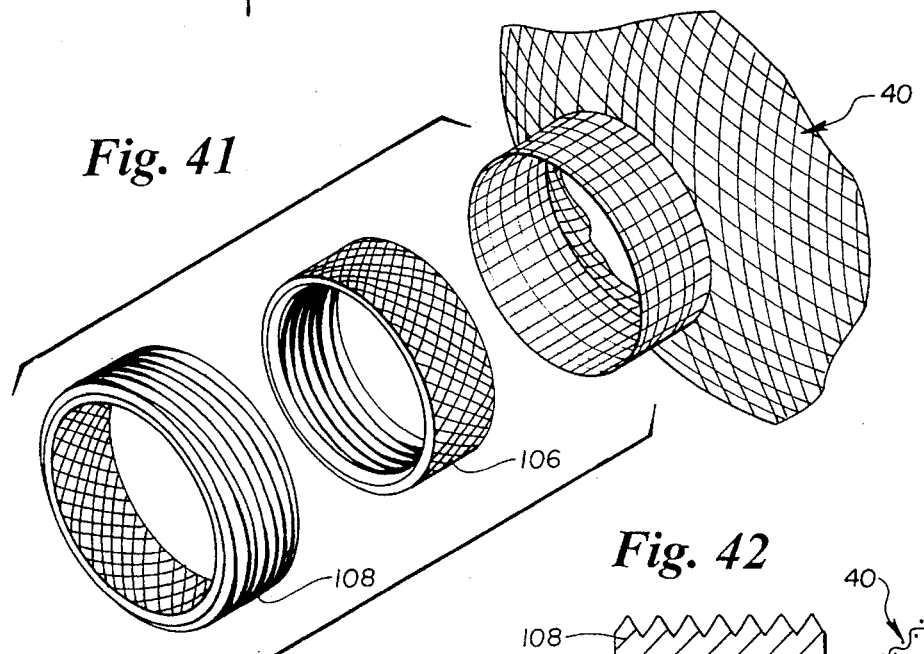
FIG. 41 shows the fill opening of FIG. 40 exploded.
Figure 42:
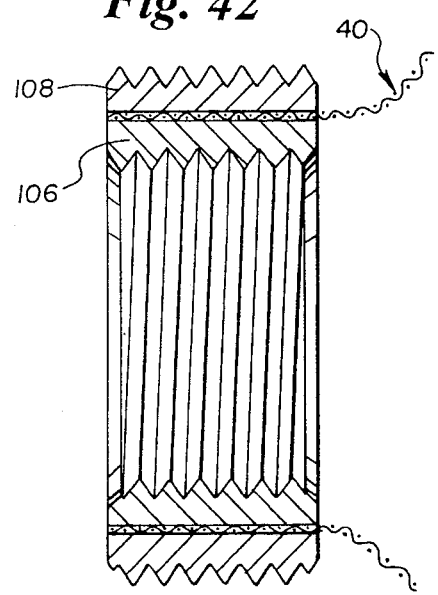
FIG. 42 shows a cross-sectional view through line 42—42 of FIG. 40.
Figure 43:
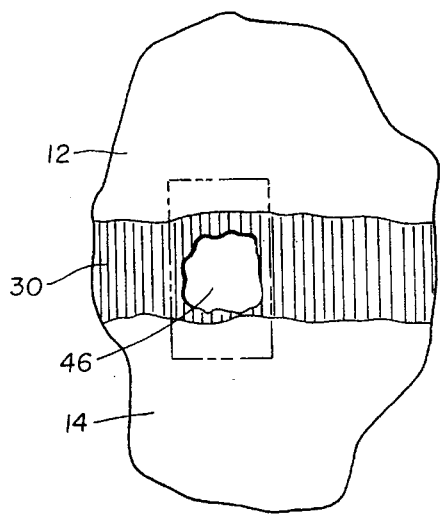
FIG. 43 shows an annulus with an opening to close.

With reference to FIGS. 40–42, the bag 40 is shown with a formed fill opening 48 in which the fabric or other material of the bag is trapped between an inner ring 106 and an outer ring 108 to provide a threaded opening as shown. Outer ring 108 is threaded so it may be closed with a mating cap. The connection between the parts of FIGS. 40–42 may be through the application of selective heating and cooling, such that each ring is taken to a set temperature at which expansion or contraction from its normal state occurs. At that time, the fabric of the bag is sandwiched therebetween and the parts are allowed to rebound to their normal shapes, causing a tight fit as shown.

Figure 44:
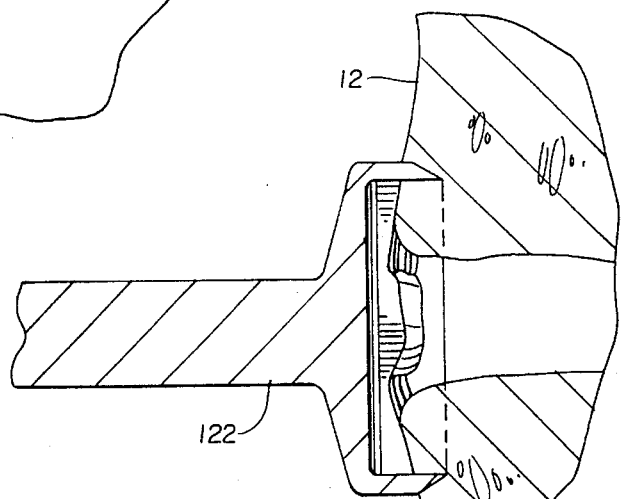
FIG. 44 shows a punch removing damaged annulus material down to raw bleeding bone.
Figure 45:
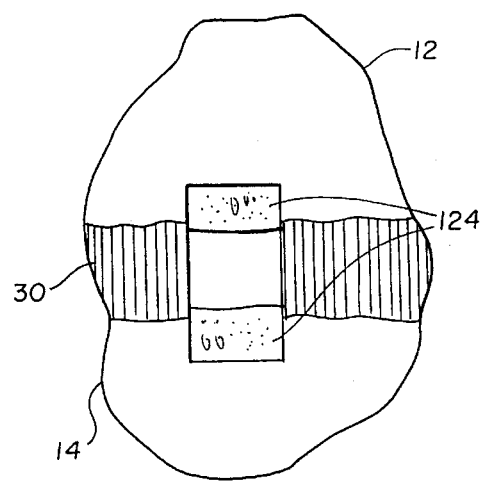
FIG. 45 shows the annulus ready to accept a patch.
Figure 47:
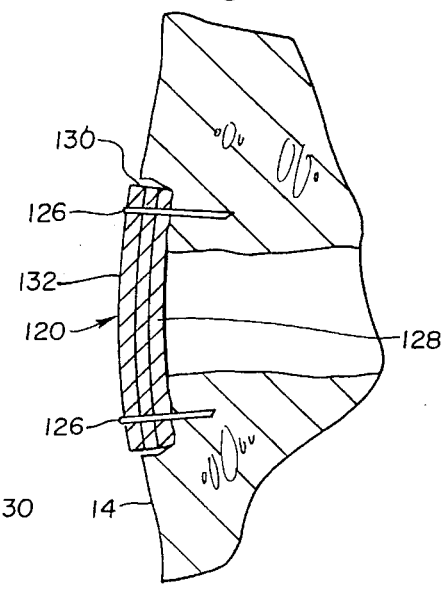
FIG. 47 is a cross-sectional view of FIG. 46 showing the staples and patch.
Figure 46:
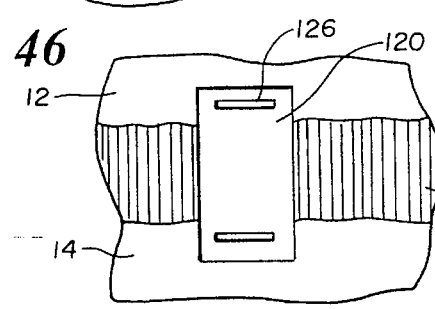
FIG. 46 shows a patch stapled in place.

With reference to FIGS. 43–47, it will be seen that an opening or hole in the annulus 30 may be repaired. In FIG. 46, the opening in the annulus may be closed off with a repair patch 120. FIG. 44 shows a punch 122 which cuts out a pre-defined opening exposing bleeding bone 124. A biological graft of connective tissue 120 such as bovine pericardium or human fascia which may be strengthened with polymer layers is fashioned and placed over the defined opening. Staples 126 may be used to connect the patch 120 in place. The patch 120 may be formed from multiple layers, with a first porous layer 128 through which blood and other products may pass, a second layer 130 defining strips to form channels and a third over-layer 132. The channels would allow ingrowth of connective tissue to complete the repair. Before the patch 120 is positioned, dura is covered with fat. This provides a barrier to excessive scar formation. Such a patch may prevent recurrent disc hernia after routine disc excision.

Figure 48:
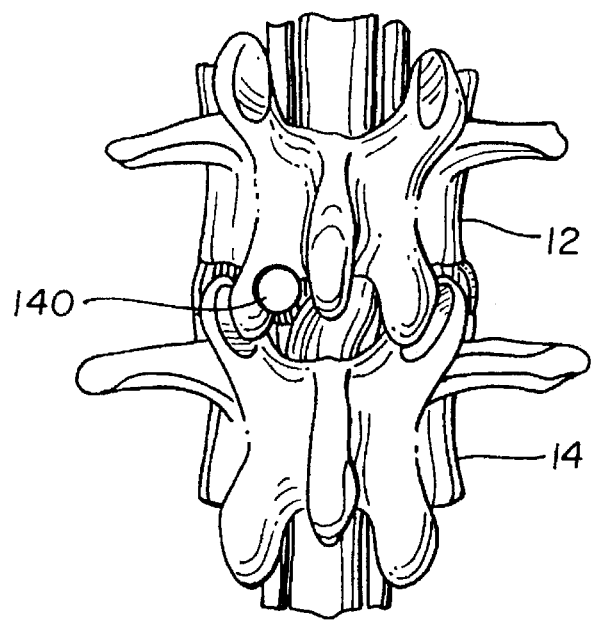
FIG. 48 is a view of a spinal segment showing an opening to seal.
Figure 49:
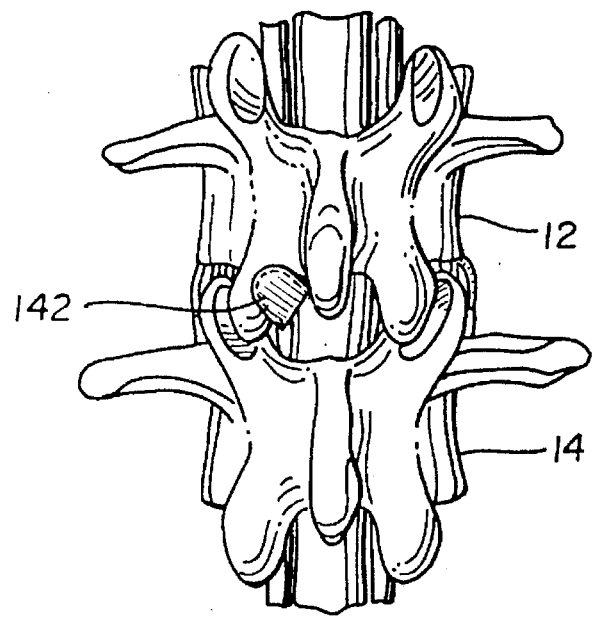
FIG. 49 shows the spinal segment of FIG. 48 with a repair patch in place.
Figure 50:
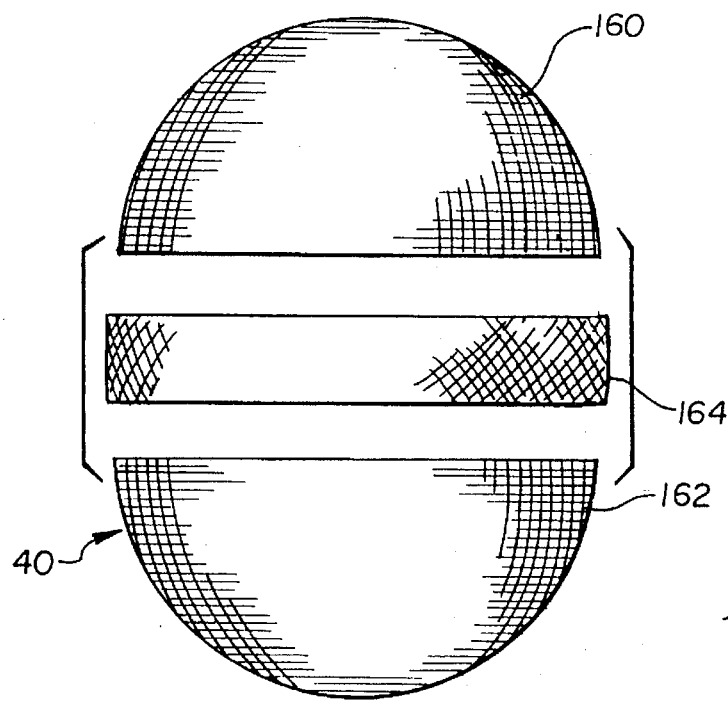
FIG. 50 shows an alternative method to form the bag of the invention showing an exploded bag.
Figure 51:
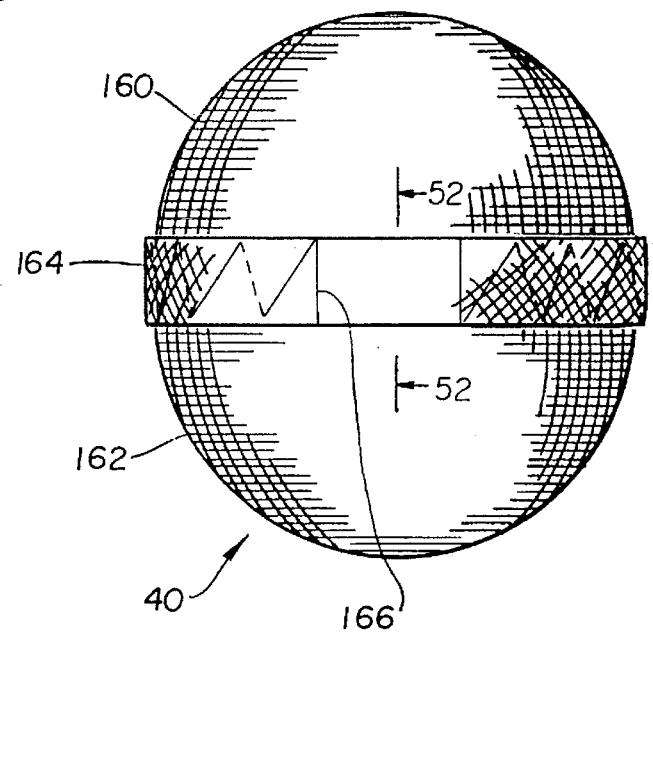
FIG. 51 shows the bag of FIG. 50 assembled.

FIGS. 48 and 49 show that an opening 140 cut into the distal surface of vertebra 12 may be closed in a manner similar to that shown in FIGS. 43–47. The opening may be closed by cutting into bone to provide a surface for a patch 142 which may then be secured by staples 126. Underlayers of fat as a cushion may be added as indicated.

Figure 52:
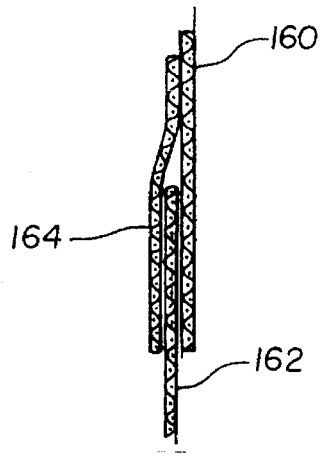
FIG. 52 is a sectional view taken along line 52—52 of FIG. 51.

FIGS. 50–56 show a bag 10 construction in which the bag 40 is formed from two hemispheres 160, 162 and a central band 164. As shown in FIG. 52, the layers of hemispheres 160, 162 and band 164 overlap to provide a three-ply equatorial band region which will be stiffer than other areas of the bag 40. The bag is completed by sealing, as by sutures 166 through each layer. An unsealed region is used to introduce an insertion tool 90.

Figure 53:
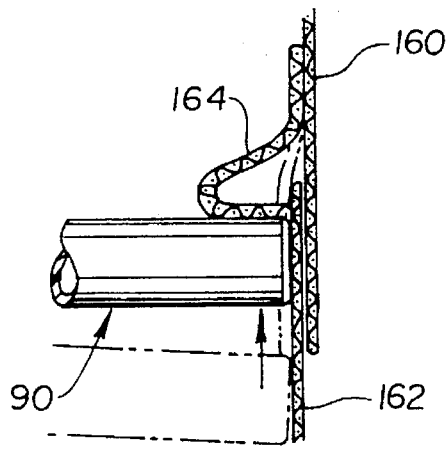
FIG. 53 shows filling of the bag by an insertion tool.
Figure 54:
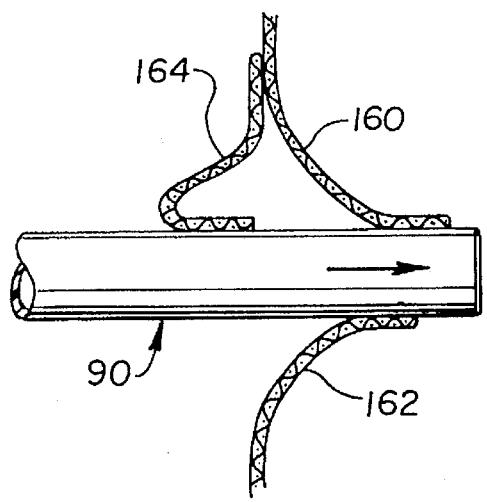
FIG. 54 shows filling of the bag by an insertion tool with the tool entering the bag.
Figure 55:
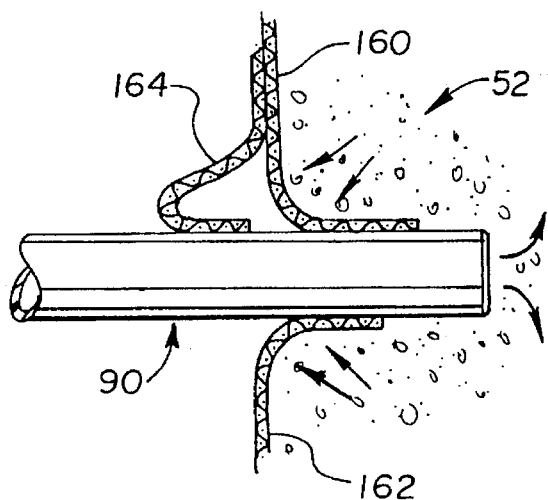
FIG. 55 shows the bag inflating with the bag expanding to self-seal.
Figure 56:
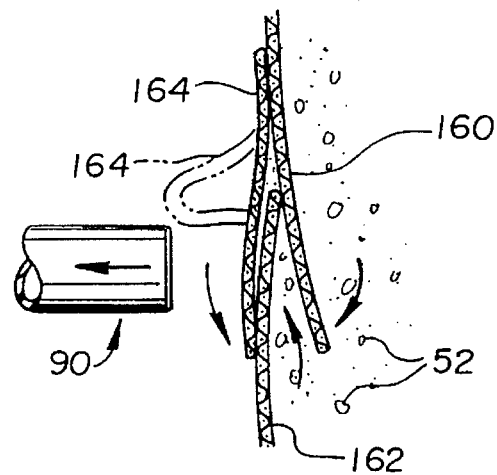
FIG. 56 shows the insertion tool removed with internal pressure in the bag closing the insertion opening.

This unique design of the bag as shown in FIGS. 50–56 allows easy filling and self-sealing due to the internal pressure in the filled bag 40. As shown in FIG. 53, the insertion tool 90 is simply pushed through the triple fabric layers of hemispheres 160, 162 and band 164. By comparing FIGS. 54, 55 and 56, it will be readily seen that internal pressure generated as the bag fills with fill material 52 causes fabric edges 160, 162 to bow back and when the tool 90 is withdrawn, the edges reseal as shown in FIG. 56. This fill port is very simple, and only involves passing the insertion tool 90 through an unsealed area (or where seal is opened). The construction will normally try to self-seal when pressure is applied from the bag interior, as by filling.

RESULTS

Experiments in my laboratory have confirmed the fact that inflation of the prototype device using morselized bone graft prepared in a bone mill, under proper pressure of inflation, results in a remarkable change in the mechanical properties of the implant. Namely, the device becomes extremely rigid and relatively incompressible. This characteristic of the inflated condition explains the remarkable stability that is produced in the motion segment. Based on the teachings of several surgeons, we know that densely compacted bone graft, inserted into the properly prepared vertebral interspace, will result in the growth of certain tissues into and through the graft material, eventually resulting in a fibrous or bony fusion, effectively cementing the vertebral bones into a stable union that is known to be desirable in terms of reducing spinal pain and improving function.

The fabric device of the invention would also produce this stabilizing fusion. Furthermore, the fabric encased graft implant would have certain advantages over the mere injection of graft material into the intervertebral space without the encasing fabric. Namely, the fabric encased graft would have less tendency to flow out of the intervertebral cavity, since its contents would be retained by the walls of the fabric bag. Additionally, the encased graft would retain its mechanical function for a much longer time, providing stability to the motion segment and thus providing an ideal milieu for tissue bonding between the vertebral bodies.

Steps in the Process of Spinal Stabilization Using this Method

Step #1. Expose and remove the diseased nucleus and/or inner annulus by one of several means, including the use of the Kuslich Expandable Reamer, U.S. Pat. No. 5,015,255, the disclosure of which is incorporated herein by reference.

Step #2. Insert the unexpanded device (Expandable Fabric Bag Device) (EFBD) into the cavity between the vertebral bones.

Step #3. Prepare material to be inserted (or injected into the EFBD). This material might be one or more of the following, or any other biocompatible material judged to have the desired physiologic response:

A) Morselized bone graft, cortical, cancellous, or cortico-cancellous, including autograft, allograft, or xenograft.

B) Any bone graft substitute or combination of bone graft substitutes, or combinations of bone graft and bone graft substitutes, or bone inducing substances, including but not limited to:
Hydroxyapatite
Bone morphogenic protein
Calcified or decalcified bone derivative Step #4. Inject or insert the graft material into the device using sufficient pressure to fill the internal cavity of the device, thus producing rigidity and tension on the wall of the device.

Step #5. Closure of the fill opening to prevent egress of inflation material.

The devices and methods of the invention may be used anytime in which a disc is being repaired or replaced. The device may be added to a cavity formed when the nucleus of the disc is excised, thereby restoring the proper height and cushioning. If the disc is to be replaced, portions of the disc may be left to confine the inventive device which allows fibrous growth and functions as a repaired disc. While the disclosure has primarily shown generally spherical bags, it is contemplated that any shape, including FIG. 8 shaped bags, donut shaped bags and the like are usable herein.

In addition, the device of the invention may be used in conjunction with other devices. For example, the device of my U.S. Pat. No. 5,059,193 may be incorporated inside of the inventive bag of this invention if the advantages of that invention are desired in addition to those of the present invention.

While this invention may be embodied in many different forms, there are shown in the drawings and described in detail herein specific preferred embodiments of the invention. The present disclosure is an exemplification of the principles of the invention and is not intended to limit the invention to the particular embodiments illustrated.

This completes the description of the preferred and alternate embodiments of the invention. Those skilled in the art may recognize other equivalents to the specific embodiment described herein which equivalents are intended to be encompassed by the claims attached hereto.

What is claimed is:

1. A device for use in stabilizing a spinal motion segment comprising:

a generally hollow, flexible bag adapted for expansion solely by the introduction of graft material, said bag being further characterized by the absence of any other expansion means, said bag including at lest one fill opening into which biological fill material for promoting bony or fibrous union may be inserted, said bag being filled with biological fill material to a rigid state, said flexible bag including a plurality of pores, said pores being sized to allow ingress and egress of liquids, solutions, small particle suspensions and ingrowth of bony trabeculae or fabrous elements into and through said device when said device is positioned in a hollowed region of an intervertebral space, said pores being sized to retain said fill material within said bag; said bag further including closure means for closing said fill opening to prevent egress of said fill material from said bag, wherein said bag is generally spherical in shape, having an equator defined by a line extending circumferentially around a periphery of the spherical shape, an axis and an equatorial band, said equatorial band having greater rigidity than the remainder of said bag causing a force to be directed in a predefined direction.

2. The device of claim 1 wherein said band has a height that approximates a height of a normal interdiscal interval at or near a margin of a disc.

3. The device of claim 2 wherein said band is formed of a material with substantially less resilience than material forming the remainder of said bag.

* * * * *

UNITED STATES PATENT AND TRADEMARK OFFICE
CERTIFICATE OF CORRECTION

PATENT NO. : 5,571,189
DATED : Nov. 5, 1996
INVENTOR(S) : Stephen D. Kuslich

It is certified that error appears in the above-indentified patent and that said Letters Patent is hereby corrected as shown below:

Col. 12, line 62, delete "lest" and insert -- least --

Signed and Sealed this

Fourth Day of February, 1997

Attest:

BRUCE LEHMAN

*Attesting Officer*  *Commissioner of Patents and Trademarks*